US012431499B2

(12) United States Patent
Lévesque-Bélanger et al.

(10) Patent No.: US 12,431,499 B2
(45) Date of Patent: Sep. 30, 2025

(54) SULFUR-CONTAINING COMPOUNDS AND POLYMERS AND THE USE THEREOF IN ELECTROCHEMICAL CELLS

(71) Applicant: HYDRO-QUÉBEC, Montréal (CA)

(72) Inventors: Rachel Lévesque-Bélanger, Mercier (CA); Andrea Paolella, Montreal (CA); Jean-Christophe Daigle, Longueuil (CA); Basile Commarieu, Montréal (CA); Michel Armand, Montreal (CA); Karim Zaghib, Longueuil (CA)

(73) Assignee: HYDRO-QUÉBEC, Montreal (CA)

( * ) Notice: Subject to any disclaimer, the term of this patent is extended or adjusted under 35 U.S.C. 154(b) by 569 days.

(21) Appl. No.: 17/895,307

(22) Filed: Aug. 25, 2022

(65) Prior Publication Data

US 2023/0064888 A1 Mar. 2, 2023

Related U.S. Application Data

(62) Division of application No. 16/644,714, filed as application No. PCT/CA2018/051239 on Oct. 2, 2018, now Pat. No. 11,469,419.

(30) Foreign Application Priority Data

Oct. 2, 2017 (CA) ..................................... 2981012

(51) Int. Cl.

| | |
|---|---|
| ***H01M 4/60*** | (2006.01) |
| ***C07D 209/48*** | (2006.01) |
| ***C08G 75/14*** | (2006.01) |
| ***H01M 4/137*** | (2010.01) |
| ***H01M 4/38*** | (2006.01) |
| ***H01M 4/62*** | (2006.01) |
| ***H01M 10/052*** | (2010.01) |
| ***H01M 10/0565*** | (2010.01) |
| ***H01M 10/0567*** | (2010.01) |
| ***H01M 10/0568*** | (2010.01) |
| ***H01M 10/0569*** | (2010.01) |

(52) U.S. Cl.

CPC .......... *H01M 4/602* (2013.01); *C07D 209/48* (2013.01); *C08G 75/14* (2013.01); *H01M 4/137* (2013.01); *H01M 4/38* (2013.01); *H01M 4/623* (2013.01); *H01M 4/625* (2013.01); *H01M 10/052* (2013.01); *H01M 10/0565* (2013.01); *H01M 10/0567* (2013.01); *H01M 10/0568* (2013.01); *H01M 10/0569* (2013.01); *H01M 2300/0025* (2013.01); *H01M 2300/0082* (2013.01); *H01M 2300/0085* (2013.01)

(58) Field of Classification Search

None

See application file for complete search history.

(56) References Cited

U.S. PATENT DOCUMENTS

| | | | | |
|---|---|---|---|---|
| 4,716,216 | A | 12/1987 | Takekoshi et al. | |
| 2002/0055040 | A1 | 5/2002 | Mukherjee et al. | |
| 2003/0157409 | A1* | 8/2003 | Huang ................ | H01M 50/426 429/231.95 |
| 2015/0030331 | A1 | 1/2015 | Salsi et al. | |
| 2015/0079473 | A1* | 3/2015 | Kang .................. | H01M 4/1391 429/223 |
| 2020/0287218 | A1 | 9/2020 | Lévesque-Bélanger et al. | |

FOREIGN PATENT DOCUMENTS

| | | | |
|---|---|---|---|
| CA | 1123543 | A | 5/1982 |
| DE | 4243463 | A1 | 3/1994 |
| EP | 0213573 | A2 | 3/1987 |
| EP | 0387106 | A1 | 9/1990 |
| EP | 0449117 | A2 | 10/1991 |
| JP | 2000511342 | A | 8/2000 |
| JP | 2015518329 | A | 6/2015 |
| WO | 9954363 | A1 | 10/1999 |

OTHER PUBLICATIONS

Office Action (Notice of Reasons for Rejection) issued on Dec. 19, 2022, by the Japanese Patent Office in corresponding Japanese Patent Application No. 2020-518728 and an English Translation of the Office Action. (5 pages).

International Search Report (PCT/ISA/210) and translation and Written Opinion (PCT/ISA/237) mailed on Jan. 7, 2019, by the Canadian Patent Office as the International Searching Authority for International Application No. PCT/CA2018/051239.

Extended European Search Report dated May 26, 2021, issued by the European Patent Office in corresponding European Application No. 18864901.6-1107, with English Translation. (10 pages).

Armand, M. et al., "Building better batteries", Nature, vol. 451, Feb. 7, 2008.

Buck, et al., "Non-Destructive In Situ Analysis Interface Processes and Thin Film Growth", J. Adhesion, 1996, vol. 58, pp. 227-241.

Chen, H. et al., "From Biomass to a Renewable LiXC6O6 Organic Electrode for Sustainable Li-Ion Batteries", ChemSusChem, 2008, vol. 1, pp. 348-355.

Chung, W. J. et al., "The use of elemental sulfur as an alternative feedstock for polymeric materials", Nature Chemistry, Macmillan Publishers Limited, vol. 5, Jun. 2013, pp. 518-524.

Gaspert, et al., "Optically Active Trisulphides and Tetrasulphides Related to L-Cysteine", Croatica Chemica Acta, 1960, vol. 32, pp. 85-90.

(Continued)

*Primary Examiner* — Anca Eoff

(74) *Attorney, Agent, or Firm* — Womble Bond Dickinson (US) LLP

(57) ABSTRACT

The present technology relates to a sulfur-containing polymer or organic compound for use in a positive electrode material, especially in lithium batteries. More specifically, the use of this sulfur-containing polymer or compound as an active electrode material makes it possible to combine sulfur and an active organic cathode material. The present technology also relates to the use of the sulfur-containing polymer or organic compound as defined herein as a solid polymer electrolyte (SPE) or as an additive for electrolyte, especially in lithium batteries.

23 Claims, 10 Drawing Sheets

(56) References Cited

OTHER PUBLICATIONS

Hoefling, A. et al., "A sulfur-eugenol allyl ether copolymer: a material synthesized via inverse vulcanization from renewable resources and its application in Li—S batteries", Mater. Chem. Front., 2017, vol. 1, pp. 1818-1822.
Hyun, S. et al., "Rational Sulfur Cathode Design for Lithium-Sulfur Batteries: Sulfur-Embedded Benzoxazine Polymers", ACS Energy Lett., 2016, vol. 1, pp. 566-572.
Le Gall, T et al., "Poly(2,5-dihydroxy-1,4-benzoquinone-3,6-methylene): a new organic polymer as positive electrode material for rechargeable lithium batteries", Journal of Power Sources, vol. 119-121, (2003), pp. 316-320.
Liang, Y. et al., "Organic Electrode Materials for Rechargeable Lithium Batteries", Adv. Energy Mater., 2012, vol. 2, pp. 742-769.
Shukla, S et al., "Cardanol benzoxazine-Sulfur Copolymers for Li—S batteries: Symbiosis of Sustainability and Performance", ChemistrySelect, 2016, vol. 3, pp. 594-600.
Wang, J_Z, et al., "Sulfur-graphene composite for rechargeable lithium batteries", Journal of Power Sources, vol. 196 (2011), pp. 7030-7034.
Zeng, R. et al., "Polycarbonyl(quinonyl) organic compounds as cathode materials for sustainable lithium ion batteries", Electrochimica Acta, vol. 146, (2014), pp. 447-454.
Zhou, W. et al., "Yolk-Shell Structure of Polyaniline-Coated Sulfur for Lithium-Sulfur Batteries", J. Am. Chem. Soc., 2013, vol. 135, pp. 16736-16743.

* cited by examiner

SULFUR-CONTAINING COMPOUNDS AND POLYMERS AND THE USE THEREOF IN ELECTROCHEMICAL CELLS

CROSS REFERENCE TO RELATED APPLICATIONS

This application is a divisional of U.S. application Ser. No. 16/644,714, filed on Mar. 5, 2020, which is a U.S. National Stage of International Application No. PCT/CA2018/051239, filed on Oct. 2, 2018, which claims the benefit of Canadian Application No. 2,981,012, filed on Oct. 2, 2017. The entire contents of each of U.S. application Ser. No. 16/644,714, International Application No. PCT/CA2018/051239, and Canadian Application No. 2,981,012 are hereby incorporated herein by reference in their entirety.

TECHNICAL FIELD

The present application relates to the field of polymers and oligomers for use as electrochemically active material in a positive electrode, as solid polymer electrolyte (SPE), or as additive for an electrolyte, in particular in lithium batteries.

BACKGROUND

A global environmental awareness influences a large number of scientists to find answers to the problem of greenhouse gases and their impacts on our planet. Knowing that transportation plays a major role in greenhouse gas emissions, the electrification of transportations is definitely part of the solution to global warming. It is therefore important to design new battery materials that are greener, more affordable, safer and, that offer performance close to that of fossil fuels (such as autonomy and power).

Organic cathodes are prime candidates for the production of batteries that can meet the demand with respect to energy storage. An advantage of these materials is the synthesis temperature which is significantly lower than that of intercalation materials (Armand et al. *Nature,* 2008, 451, 652). In addition, they are composed of abundant elements and offer excellent electrochemical performance (Le Gall et al. *Journal of Power Sources,* 2003, 316-320). On the other hand, their greatest disadvantage relates to the dissolution of the active material in the electrolyte, which greatly affects the stability of the battery (Chen et al. *ChemSusChem.,* 2008, 1, 348-355). Electrochemically active organic polymers may make it possible to inhibit or reduce the dissolution of the active material in order to obtain a material with greater cyclability (Zeng et al. *Electrochimica Acta,* 2014, 447-454).

Elemental sulfur is also a candidate for the production of batteries with high energy density. Indeed, lithium sulfur (Li—S) batteries are very promising considering the advantages offered by this element, i.e. a high capacity of 1675 mAh/g and a great abundance, the latter being attributed to the fact that sulfur is a petroleum refinery by-product (Hyun et al. *ACS Energy Letters,* 2016, 1, 566-572). However, Li—S batteries also has several disadvantages, including the dissolution of the polysulfides ($Li_2S_x$, x=4-8) produced by the reduction of sulfur during cycling. In addition, once dissolved, the polysulfides are involved in a phenomenon called "shuttle effect" which destabilizes the lithium surface (anode). This phenomenon leads to a reduction in stability as well as a low coulombic efficiency (Zhou et al. *J. Am. Chem. Soc.* 2013, 135, 16736-16743).

One strategy used to solve this problem involves the encapsulation of sulfur particles. For example, Zhou et al. (*J. Am. Chem. Soc.* 2013, 135, 16736-16743) coated sulfur with polyaniline (PANI) to immobilize the polysulfides inside this shell. The encapsulation of sulfur then makes it possible to increase the battery stability. However, the addition of this element limits the quantity of sulfur in the active material to only 58% by weight, which means that 42% by weight of the material consists of an electrochemically inactive material, thereby reducing the charge density of the electrode material. Although this strategy still allows to obtain a coulombic efficiency greater than 97%, it still has limited long-term cyclability.

The synthesis of carbon-sulfur composites has also been presented. For example, Wang et al. (*Journal of Power Sources,* 2011, 7030-7034) have synthesized a graphene-sulfur composite. This new material makes it possible not only to increase the intrinsic conductivity, but also to achieve an initial capacity that is almost equivalent to the theoretical value. However, the presence of graphene does not allow to inhibit the phenomenon of polysulphides dissolution, this material having a capacity loss equivalent to that of sulfur itself.

The copolymerization of elemental sulfur with one or more organic monomers has also been explored in order to obtain a sulfur-rich polymer. When sulfur is heated above 159° C., a ring opening of the ($S_8$) cycle occurs thereby generating a diradical which can undergo radical polymerization. Chung et al. (*Nature Chemistry,* 2013, 5, 518-524) have developed a sulfur-rich copolymer for Li—S batteries. Elemental sulfur was copolymerized with different percentages of 1,3-diisopropenylbenzene (DIB) by inverse vulcanization. The copolymerization allows to create a matrix that can limit polysulfides dissolution. Their electrochemical results show great coulombic efficiency as well as good capacity retention. However, as presented above, the organic monomer used is electrochemically non-active, which results in the presence of an inert mass and consequently a decrease in energy density.

Consequently, there is therefore a need for the development of new electrode materials, for example, combining some advantages of the preceding materials while excluding at least one of their disadvantages.

SUMMARY

According to a first aspect, the present description relates to a polymer of Formula I:

Formula I

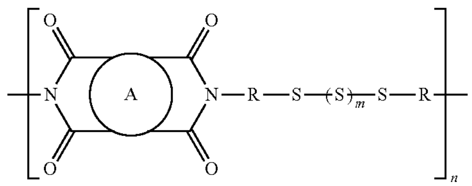

wherein:

A is selected from unsaturated groups allowing the delocalization of electrons, for example, substituted or unsubstituted aryl and heteroaryl groups, and their fused or unfused polycyclic counterparts;

R is a substituted or unsubstituted organic linking group selected from linear or branched $C_{2-6}$alkylene, linear or branched $C_{2-6}$alkyleneoxy, linear or branched $C_2$-6alkyleneglycol, linear or branched $C_{2-6}$alkyleneoxy$C_{2-}$ $_{6}$alkylene, linear or branched poly($C_{2-6}$alkyleneglycol), $C_{6-12}$arylene, $C_{3-12}$cycloalkylene, $C_{5-12}$heteroarylene, and $C_{3-12}$heterocycloalkylene;

m represents the average number of sulfur atoms inserted into the disulfide bond of the polymer links and cannot be zero, i.e. $m>0$, for example, $0<m\leq 8$, or $1\leq m\leq 6$, or $1\leq m\leq 4$; and n represents the average number of units in the polymer, for example, n may be in the range of 2 to 500, or of 5 to 300.

According to one embodiment, A is selected from benzene, naphthalene, perylene and biphenyl groups. For example, A is a benzene group, the polymer being of Formula I(a):

Formula I(a)

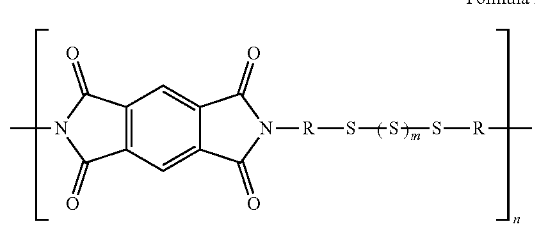

wherein R, m and n are as defined herein.

According to another embodiment, R is selected from the groups benzene, ethylene, propylene, poly(ethylene glycol), poly(propylene glycol), and copolymers of ethylene glycol and propylene glycol.

An example of a polymer is also exemplified by Formula I(b):

Formula I(b)

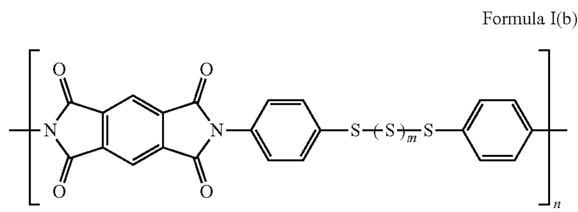

wherein m and n are as defined herein.

According to another aspect, the present description relates to a compound of Formula II:

Formula II wherein A and R are as defined herein, and m represents the number of sulfur atoms inserted into the disulfide bond of the compound, for example, $m>0$, for example, $0<m\leq 8$, or $1\leq m\leq 6$, or $1\leq m\leq 4$.

An example of this compound is represented by Formula II(a):

Formula II(a)

wherein R and m are as defined herein.

Another example of the compound is illustrated by Formula II(b):

Formula II(b)

wherein m is as defined herein.

According to another aspect, the present description relates to an electrode material comprising a polymer or a compound as defined herein. For example, the electrode material further comprises a conductive material, a binder, or a combination of both. The electrode material may also contain free elemental sulfur ($S_x$).

According to one embodiment, the conductive material is selected from carbon black, Ketjen™ carbon, Shawinigan carbon, acetylene black, graphite, graphene, carbon fibers (such as carbon nanofibers (for example, VGCF formed in the gas phase)), carbon nanotubes, or a combination of at least two thereof.

According to one embodiment, the binder is a polymeric binder of polyether type, fluorinated polymer type, or a water-soluble binder. According to one example, the polymeric binder of polyether type is linear, branched and/or crosslinked and is based on poly(ethylene oxide) (PEO), poly(propylene oxide) (PPO), or a combination of the two (or an EO/PO co-polymer), and optionally comprises crosslinkable units. According to another example, the fluorinated polymer binder is PVDF (polyvinylidene fluoride) or PTFE (polytetrafluoroethylene). Finally, examples of water-soluble binders include SBR (styrene-butadiene rubber), NBR (acrylonitrile-butadiene rubber), HNBR (hydrogenated NBR), CHR (epichlorohydrin rubber), or ACM (acrylate rubber), optionally comprising CMC (carboxymethyl cellulose).

According to an additional aspect, the present description relates to a positive electrode comprising an electrode material as defined herein, applied on a current collector.

According to an additional aspect, the present description also relates to an electrolyte comprising a polymer as defined herein, or a compound as defined herein. According to one embodiment, the electrolyte is a liquid electrolyte comprising a salt in a solvent. According to one alternative, the electrolyte is a gel electrolyte comprising a salt in a solvent and optionally a solvating polymer. According to a second alternative, the electrolyte is a solid polymer electrolyte (SPE) comprising a salt in a solvating polymer. For example, the polymer as defined herein, or the compound as defined herein is an additive. Alternatively, the solvating polymer of the SPE is the polymer as defined herein, or the compound as defined herein. According to another embodiment, the salt is a lithium salt. According to one embodiment, the electrolyte further comprises elemental sulfur, a binder, an additive or a combination of at least two thereof.

Another aspect refers to electrochemical cells comprising a cathode, an electrolyte and an anode, wherein the cathode comprises an electrode material as defined herein. According to an alternative, these electrochemical cells comprise a negative electrode, an electrolyte and a positive electrode as defined herein. According to an alternative, these electrochemical cells comprise a cathode, an anode and an electrolyte as defined herein. The present description also refers to lithium batteries comprising such an electrochemical cell.

Finally, the present description refers to processes for manufacturing the polymers and compounds as defined herein, electrode materials, electrolyte materials, electrodes, electrolytes, and electrochemical cells comprising them. The use of these electrochemical cells is also contemplated, more particularly in portable devices, for example, mobile phones, cameras, tablets or laptops, in electric or hybrid vehicles, or in renewable energy storage.

DETAILED DESCRIPTION

Figure 1A:
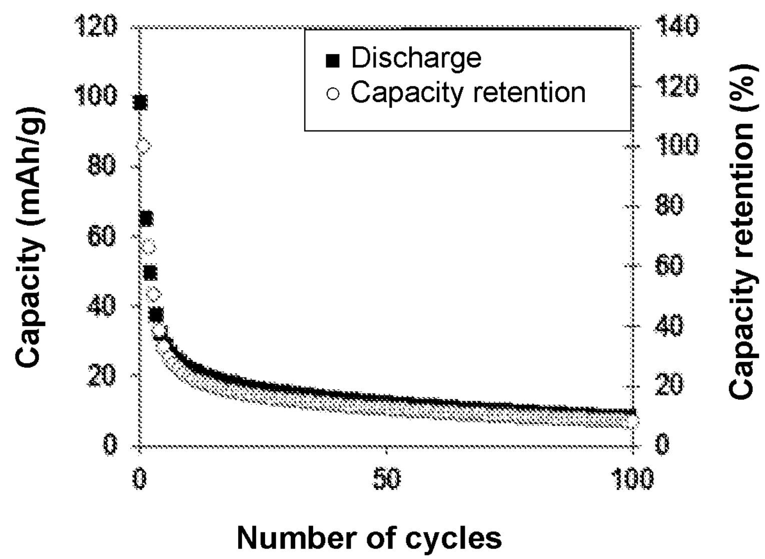
FIGS. 1A-1B present the capacity (mAh/g) and the percentage of capacity retention results as a function of the number of cycles in (A) for Cell 1 (reference) which includes polyimide disulfide and in (B) for Cell 2 which includes the polyimide-co-polysulfide including 35% by weight of sulfur.

All technical and scientific terms and expressions used herein have the same definitions as those commonly understood by the person skilled in the art relating to the present technology. The definition of some terms and expressions used is nevertheless provided below.

The term "about" as used herein means approximately, in the region of, and around. When the term "about" is used in connection with a numerical value, it modifies it, for example, above and below by a variation of 10% with respect to the nominal value. This term may also take into account, for example, the experimental error of a measuring apparatus or rounding.

When a range of values is mentioned in the present application, the lower and upper limits of the range are, unless otherwise indicated, always included in the definition.

The chemical structures described herein, are drawn according to standards of the field. Also, when an atom, such as a carbon atom, as drawn seems to include an incomplete valency, then the valency is assumed to be satisfied by one or more hydrogen atoms even though these are not explicitly drawn.

As used herein, the terms "alkyl" or "alkylene" refer to saturated hydrocarbon groups having between one and sixteen carbon atoms, including linear or branched groups. Examples of alkyl groups include, without limitation, methyl, ethyl, propyl, butyl, pentyl, hexyl, heptyl, octyl, nonyl, decyl, isopropyl, tert-butyl, sec-butyl, isobutyl, and the like. When the alkyl group is located between two functional groups, then the term alkylene can also be used, such as methylene, ethylene, propylene, and so on. The terms "$C_i$-$C_{ii}$alkyl" and "$C_i$-$C_{ii}$alkylene" refer respectively to an alkyl or alkylene group having from the number "i" to the number "ii" of carbon atom(s).

As used herein, the terms "aryl" or "arylene" refer to aromatic groups having 4n+2 π(pi) electrons, where n is an integer from 1 to 3, in a conjugated monocyclic or polycyclic system (fused or not) and having from six to twenty ring atoms. A polycyclic system includes at least one aromatic ring. The group may be directly attached or connected via a $C_1$-$C_3$alkyl group. Examples of aryl groups include, without limitation, phenyl, benzyl, phenethyl, 1-phenylethyl, tolyl, naphthyl, biphenyl, terphenyl, indenyl, benzocyclooctenyl, benzocycloheptenyl, azulenyl, acenaphthylenyl, fluorenyl, phenanthrenyl, anthracenyl, perylenyl, and the like. When the aryl group is located between two functional groups, then the term arylene may also be used. The term aryl or arylene includes substituted or unsubstituted groups. For example, the term "$C_6$-$C_n$aryl" refers to an aryl group having from 6 to the indicated "n" number of carbon atoms in the ring structure.

The term "substituted", when in association with a group refers to a group where at least one hydrogen atom has been replaced with an appropriate substituent. Non-limiting examples of substituents comprise cyano, halogen (i.e. F, Cl, Br, or I), amide, nitro, trifluoromethyl, lower alkyl, cycloalkyl, heterocycloalkyl, aryl, heteroaryl, lower alkoxy, aryloxy, benzyloxy, benzyl, alkoxycarbonyl, sulfonyl, sulfonate, silane, siloxane, phosphonato, phosphinato, and the like. These substituents can also be substituted if permissible, for example, if the group contains an alkyl group, an alkoxy group, an aryl group, etc.

The present description relates to the copolymerization of elemental sulfur with an organic monomer or the reaction of sulfur with a compound comprising a disulfide bond. For example, the present application comprises a polymer which is the result of the copolymerization of sulfur with an electrochemically active polyimide. Alternatively, the reaction of sulfur is carried out with a diimide disulfide, thereby obtaining a compound comprising a sulfide segment and an organic segment, both being electrochemically active. Not only will these compounds and polymers improve the electrochemical performance of sulfur by reducing or eliminating dissolution problems, they could also contribute to the capacity given the presence of the organic segment which is also active in the redox reaction. The electrode material comprising the polymer or compound defined herein can thus be characterized as a hybrid organosulfur positive electrode material.

For example, the polymer is a copolymer composed of an electrochemically active polyimide segment and of a polysulfide segment of the form —S—$(S)_m$—S— (where m>1). An example of a polymer is represented by Formula I:

Formula I

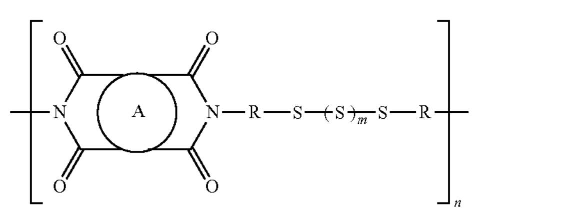

wherein:

A is selected from unsaturated groups allowing the delocalization of electrons, for example, substituted or unsubstituted aryl and heteroaryl groups, and their fused or unfused polycyclic counterparts;

R is a substituted or unsubstituted organic linking group selected from linear or branched $C_{2-6}$alkylene, linear or branched $C_{2-6}$alkyleneoxy, linear or branched $C_{2-6}$alkyleneglycol, linear or branched $C_{2-6}$alkyleneoxy$C_{2-6}$alkylene, linear or branched poly($C_{2-6}$alkyleneglycol), $C_{6-12}$arylene, $C_{3-12}$cycloalkylene, $C_{5-12}$heteroarylene, and $C_{3-12}$heterocycloalkylene;

m represents the average number of sulfur atoms inserted into the disulfide bond of the polymer links and cannot be zero, i.e. m>0, for example, 0<m≤8, or 1≤m≤6, or 1≤m≤4; and n represents the average number of units in the polymer, for example, n may be within the range of 2 to 500, or of 5 to 300.

According to one example, A may be selected from benzene, naphthalene, perylene and biphenyl groups.

For example, A is a benzene group and the polymer is of Formula I(a):

Formula I(a)

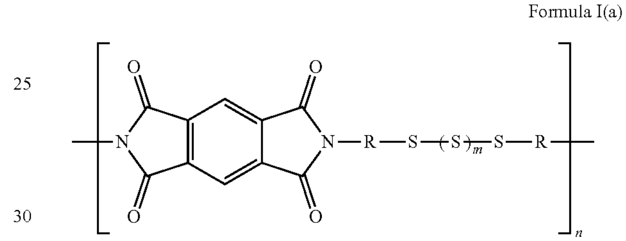

wherein R, m and n are as defined herein.

According to another example, R may be selected from the groups benzene, ethylene, propylene, poly(ethylene glycol), poly(propylene glycol), and copolymers of ethylene glycol and propylene glycol.

For example, A and R are benzene groups and the polymer is of Formula I(b) or I(c):

Formula I(b)

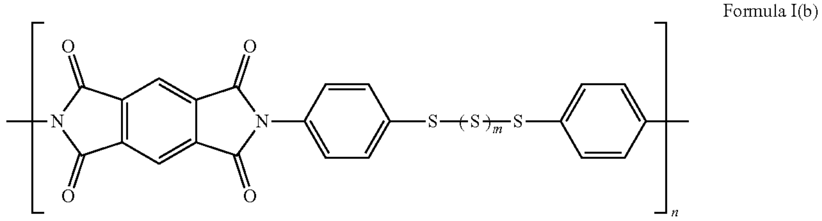

Formula I(c)

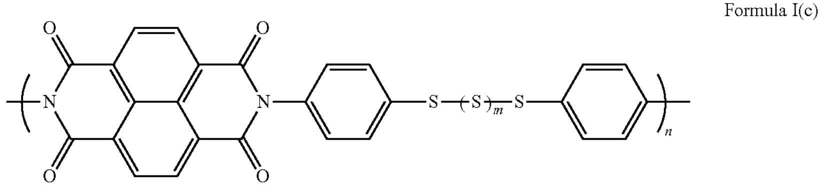

wherein, m and n are as defined herein.

According to another example, the active material is rather a compound of Formula II:

Formula II

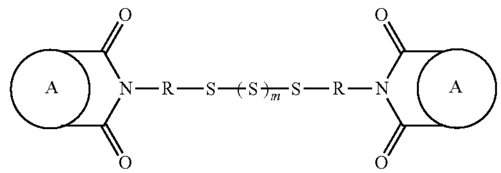

wherein A and R are as defined herein, and m represents the average number of sulfur atoms inserted into the disulfide bond of the compound, for example, m>0, for example, 0<m≤8, or 1≤m≤6, or 1≤m≤4.

For example, A is a benzene and the polymer is of Formula II(a):

Formula II(a)

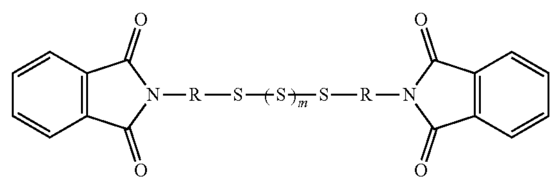

wherein, R and m are as defined herein.

For example, R is a benzene and the polymer is of Formula II(b):

Formula II(b)

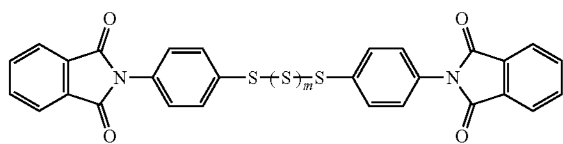

wherein, m is as defined above.

The present application also describes a process for the synthesis of polymers as defined herein and comprising an organosulfide hybrid comprising the steps of polymerization and sulfurization by reaction with elemental sulfur, these steps being carried out in any order. For example, the process comprises the following steps:

a) polymerization by polycondensation between a dianhydride and a diamine disulfide to form an electrochemically active polyimide; and b) insertion of a polysulfide segment (of —$(S)_m$— form; where m≥1), by copolymerization of the electrochemically active polyimide and of elemental sulfur $S_8$.

According to one example, the copolymer organic segment is synthesized by polycondensation between pyromellitic dianhydride (1) and 4-aminophenyl disulfide (2) to form the polyimide (3). For example, the polycondensation is carried out at a temperature of about 150° C. The copolymer can be prepared by a polymerization process as illustrated in Scheme 1:

Scheme 1

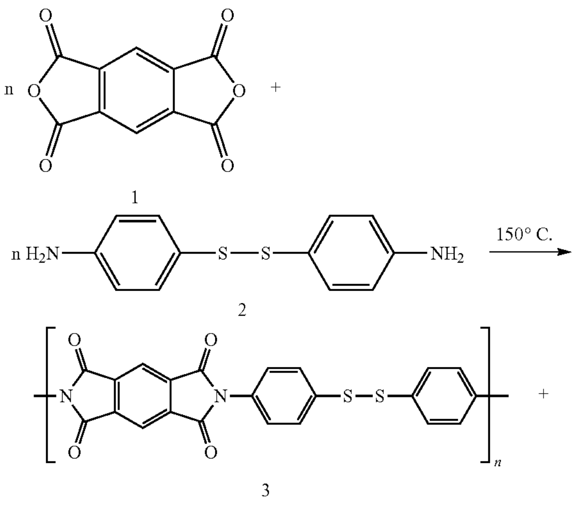

According to one example, the polysulfide segment (of the form —$(S)_m$—; where m≥1) is then inserted in the disulfide bond. The insertion can then be carried out by heating at a temperature of 150° C. or greater, or 185° C. or greater, or between 160° C. and 200° C., the electrochemically active polyimide comprising the disulfide bond as well as the elemental sulfur $S_8$. The heating step allows the opening of the elemental sulfur $S_8$ cycle to insert a polysulfide segment (of the form —$(S)_m$—; where m≥1) into the disulfide bond and form a polysulfide. Insertion of the polysulfide segment can be carried out by a process as illustrated in Scheme 2 in which the insertion of the polysulfide segment (of the form —$(S)_m$—; where m≥1) is carried out on the disulfide bond of the polyimide (3) at 185° C. in order to obtain a polyimide-co-polysulfide (4):

Scheme 2

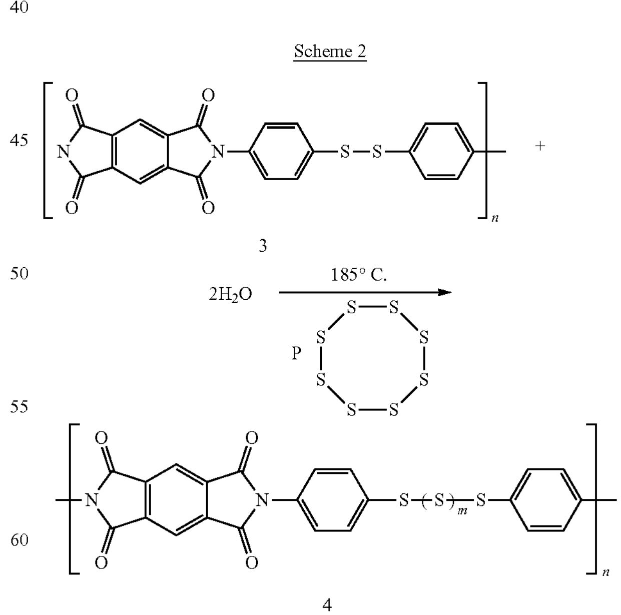

Alternatively, the present application describes a process for synthesizing polymers as defined herein and comprising an organosulfide hybrid comprising the following steps:

a) synthesis of an amino-sulfur co-monomer by the insertion of a segment (of the form —$(S)_m$—; where m≥1) forming a polysulfide carried out by polymerization of a diamine disulfide and elemental sulfur $S_8$; and b) polycondensation of the amino-sulfur co-monomer and of the dianhydride to form the polyimide.

According to one example, the polysulfide segment (of the form —$(S)_m$—; where m≥1) is inserted in the disulfide bond of the diamine disulfide. The insertion can be carried out by heating at a temperature of 150° C. or greater, or 185° C. or greater, or between 160° C. and 200° C., the elemental sulfur $S_8$ and the diamine disulfide comprising the disulfide bond. The heating step allows the opening of the elementary sulfur $S_8$ cycle to insert a polysulfide segment in the disulfide bond in order to form a polysulfide. The insertion of the polysulfide segment can be carried out by a process as illustrated in Scheme 3 in which the insertion of the polysulfide segment is carried out at 185° C. in the disulfide bond of 4-aminophenyl disulfide (2) to obtain an amino-sulfur co-monomer (3):

Scheme 3

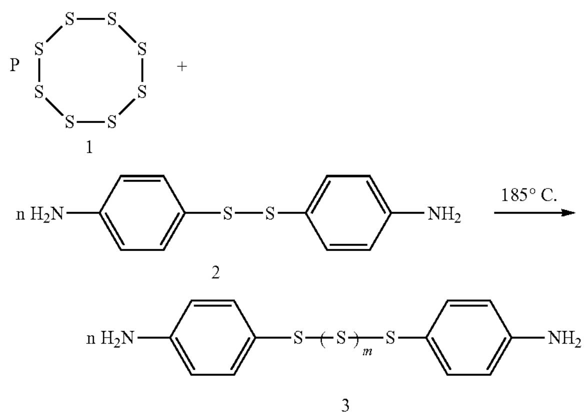

According to one example, the polymerization is then carried out by polycondensation between the amino-sulfur co-monomer (3) and the pyromellitic dianhydride (4) to form the polyimide-co-polysulfide (5). Polycondensation can be carried out, for example, at a temperature of about 150° C. The polymer can be prepared by a polymerization process as illustrated in Scheme 4:

Scheme 4

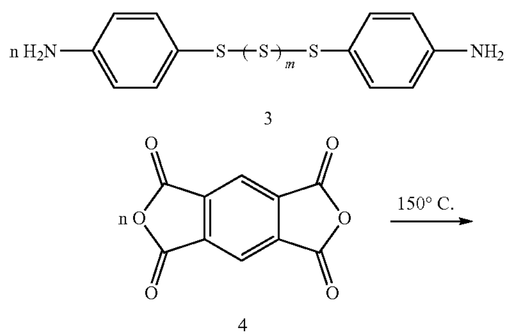

-continued

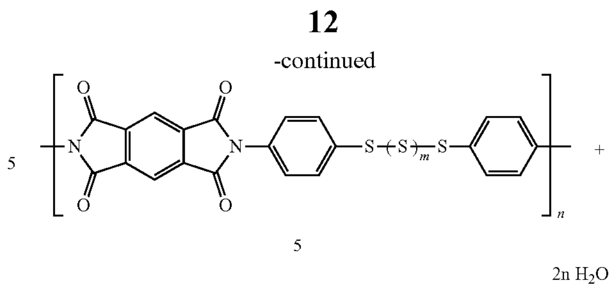

Wherein the values of m and n are determined as a function of the mass percentage of sulfur in the reaction mixture. The mass percentage of sulfur in the copolymer can vary from 0.1% to 99.9%, for example, between 5% and 95%. The polymer may also contain a certain residual amount of free elemental sulfur not inserted into the disulfide bond, particularly when a large proportion of sulfur is included in the insertion step.

The present application also proposes a positive electrode material comprising a polymer or compound as defined herein as an electrochemically active material. According to one example, the positive electrode material may further comprise an electron conductive material, a binder, or a combination thereof. The electrode material may also contain free elemental sulfur ($S_x$).

Non-limiting examples of conductive material may comprise a carbon source such as carbon black, Ketjen™ carbon, Shawinigan carbon, acetylene black, graphite, graphene, carbon fibers (such as carbon nanofibers, for example, VGCF formed in the gas phase), and carbon nanotubes, or a combination of at least two thereof. For example, the conductive material is a combination of VGCF and Ketjen™ black.

Non-limiting examples of binders comprise a polymer of linear, branched and/or crosslinked polyether type, and that may be based on poly(ethylene oxide) (PEO), poly(propylene oxide) (PPO), or a combination of the two (or an EO/PO co-polymer), and optionally comprises crosslinkable units; a fluorinated polymer such as polyvinylidene fluoride (PVDF) or polytetrafluoroethylene (PTFE); or a water-soluble binder such as styrene-butadiene rubber (SBR), acrylonitrile-butadiene rubber (NBR), hydrogenated NBR (HNBR), epichlorohydrin rubber (CHR), or acrylate rubber (ACM), and optionally comprising carboxymethyl cellulose (CMC). For example, the binder is PVDF and is dissolved in N-methyl-2-pyrrolidone (NMP) when mixed with the other components of a positive electrode material for spreading, the solvent then being removed afterwards.

According to one example, the positive electrode material can be applied on a current collector (for example, aluminum, copper). Alternatively, the positive electrode can be self-standing. For example, the current collector is aluminum.

The present application also proposes an electrochemical cell comprising at least a positive electrode material as defined herein, a negative electrode and an electrolyte. The electrolyte is then selected for its compatibility with the different components of the battery. Any type of electrolyte is contemplated, for example, liquid, gel or solid electrolytes.

The present application also proposes an electrolyte comprising a polymer as defined herein or a compound as defined herein.

According to one example, the electrolyte is a liquid electrolyte comprising a salt in a solvent. According to one alternative, the electrolyte is a gel electrolyte comprising a salt in a solvent and optionally a solvating polymer. According to another alternative, the electrolyte is a solid polymer electrolyte (SPE) comprising a salt in a solvating polymer.

Compatible electrolytes generally comprise at least one lithium salt such as lithium hexafluorophosphate ($LiPF_6$), lithium bis(trifluoromethanesulfonyl)imide (LiTFSI), lithium bis(fluorosulfonyl)imide (LiFSI), lithium 2-trifluoromethyl-4,5-dicyanoimidazolate (LiTDI), lithium 4,5-dicyano-1,2,3-triazolate (LiDCTA), lithium bis(pentafluoroethylsulfonyl)imide (LiBETI), lithium tetrafluoroborate ($LiBF_4$), lithium bis(oxalato)borate (LiBOB), lithium nitrate ($LiNO_3$), lithium chloride (LiCl), lithium bromide (LiBr), lithium fluoride (LiF), and compositions comprising them dissolved in a non-aqueous solvent (organic) or in a solvating polymer. For example, the electrolyte is LiTFSI dissolved in dimethoxyethane (DME) and 1,3-dioxolane (DOL) (DME/DOL) and include lithium nitrate (1%, $LiNO_3$).

According to another example, the electrolyte may further comprise elemental sulfur, an electrolyte binder, a separator, an additive or a combination of at least two thereof.

For example, the electrolyte binder is PVDF (polyvinylidene fluoride). For example, the electrolyte comprises between 0% by weight and 25% by weight, particularly between 0% by weight and 20% by weight, more particularly between 5% by weight and 15% by weight, even more particularly between 7% by weight and 13% by weight and ideally 10% by weight of electrolyte binder, upper and lower limits included.

Non-limiting examples of separator may include polyethylene (PE), polypropylene (PP), cellulose, polytetrafluoroethylene (PTFE), polyvinylidene fluoride (PVDF) and polypropylene-polyethylene-polypropylene (PP/PE/PP) membranes.

According to another example, the electrolyte is a solid polymer electrolyte (SPE) comprising a salt as defined herein in a solvating polymer, wherein the solvating polymer is the polymer as defined herein. For example, the SPE comprises between 60% by weight and 95% by weight, particularly between 65% by weight and 90% by weight, more particularly between 70% by weight and 85% by weight, even more particularly between 75% by weight and 85% by weight, and ideally 80% by weight of the polymer as defined herein, upper and lower limits included. For example, the SPE comprises between 5% by weight and 40% by weight, particularly between 10% by weight and 35% by weight, more particularly between 15% by weight and 30% by weight, more particularly between 15% by weight and 25% by weight, and ideally 20% by weight of salt, upper and lower limits included.

The present application also proposes an electrochemical cell comprising a cathode, an anode and an electrolyte as defined herein. The present application also contemplates an electrochemical cell comprising a cathode, an anode and an electrolyte, wherein the electrolyte and the cathode are as defined herein.

According to another aspect, an electrochemical cell of the present application is comprised in a lithium battery. For example, the lithium battery is a lithium-sulfur battery.

According to another aspect, the electrochemical cells of the present application are used in portable devices, for example, mobile phones, cameras, tablets or laptops, in electric or hybrid vehicles, or in renewable energy storage.

EXAMPLES

The following examples are illustrative and should not be construed as further limiting the scope of the present invention as described.

Example 1—Synthesis of Organosulfur Hybrid Active Electrode Materials a) Copolymerization of Pyromellitic Dianhydride, 4-Aminophenyl Disulfide and Sulfur (5% by Weight)

The synthesis of the electrode material was carried out in a 25 mL flask equipped with a magnetic bar. The active electrode material was prepared by combining 0.085 g of elemental sulfur $S_8$ (0.33 mmol) and 0.745 g of 4-aminophenyl disulfide (3 mmol). The flask was then sealed and placed under a flow of inert gas ($N_2$). Once the atmosphere of the flask was purged, the mixture was heated to a temperature of 185° C. under constant stirring at 500 rpm for about 30 minutes, until a homogeneous liquid was obtained. The mixture was then cooled to a temperature of 150° C. and the sealed cap was then removed to add 0.654 g of pyromellitic dianhydride (3 mmol) previously dissolved in an organic solvent, N, N-dimethylformamide (DMF). The flask containing the mixture was then covered up and kept at a temperature of 150° C. under stirring (500 rpm) for a period of 26 hours. The mixture was then cooled. The solid thus produced was recovered, washed with tetrahydrofuran (THF) and dried under vacuum in order to sublimate the unreacted sulfur. Finally, the percentage of sulfur in the active electrode material (polymer) produced was determined by elemental analysis. The active electrode material of the present example comprised 5% of sulfur.

b) Copolymerization of Pyromellitic Dianhydride, 4-Aminophenyl Disulfide and Sulfur (25% by Weight)

The synthesis of this active electrode material was carried out according to the process presented in Example 1(a). The masses of elemental sulfur $S_8$ and 4-aminophenyl disulfide for the synthesis of the amino-sulfur co-monomer were respectively 0.309 g (1.206 mmol) and 0.447 g (1.8 mmol) and the mass of pyromellitic dianhydride for the polycondensation was of 0.393 g (1.8 mmol). The active electrode material thus produced comprised 25% by weight of sulfur as determined by elemental analysis.

c) Copolymerization of Pyromellitic Dianhydride, 4-Aminophenyl Disulfide and Sulfur (35% by Weight)

The synthesis of this active electrode material was carried out according to the process presented in Example 1 (a). The masses of elemental sulfur $S_8$ and 4-aminophenyl disulfide for the synthesis of the amino-sulfur co-monomer were respectively 1.033 g (4.026 mmol) and 1 g (4.026 mmol) and the mass of pyromellitic dianhydride for the polycondensation was 0.878 g (4.026 mmol). The active electrode material thus produced comprised 35% by weight of sulfur as determined by elemental analysis.

d) Copolymerization of Pyromellitic Dianhydride, 4-Aminophenyl Disulfide and Sulfur (63% by Weight)

The synthesis of this active electrode material was carried out according to the process presented in Example 1(a). The masses of elemental sulfur $S_8$ and 4-aminophenyl disulfide for the synthesis of the amino-sulfur co-monomer were respectively 2.463 g (9.6 mmol) and 0.397 g (1.6 mmol) and the mass of pyromellitic dianhydride for the polycondensation was of 0.349 g (1.6 mmol). The active electrode material thus obtained comprised 63% by weight of sulfur as determined by elemental analysis.

e) Copolymerization of Pyromellitic Dianhydride, 4-Aminophenyl Disulfide and Sulfur (95% by Weight)

The synthesis of this active electrode material was carried out according to the process presented in Example 1 (a). The masses of elemental sulfur $S_8$ and 4-aminophenyl disulfide for the synthesis of the amino-sulfur co-monomer were respectively 8.978 g (35 mmol) and 0.248 g (1 mmol) and the mass of pyromellitic dianhydride for the polycondensation was of 0.218 g (1 mmol). The active electrode material thus produced comprised 95% by weight of sulfur as determined by elemental analysis.

f) Copolymerization of 1,4,5,8-Naphthalenetetracarboxylic Dianhydride, 4-Aminophenyl Disulfide and Sulfur (20% by Weight)

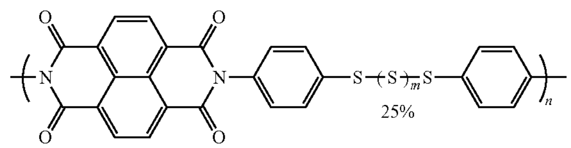

The synthesis of the electrode material was carried out in a 25 mL flask equipped with a magnetic bar. The active electrode material was prepared by combining 0.923 g of elemental sulfur $S_8$ (3.6 mmol) and 0.447 g of 4-aminophenyl disulfide (1.8 mmol). The flask was then sealed and placed under a flow of inert gas ($N_2$). Once the atmosphere of the flask was purged, the mixture was heated to a temperature of 185° C. under constant stirring at 500 rpm for about 30 minutes, until a homogeneous liquid was obtained. The mixture was then cooled to a temperature of 150° C. and the sealed cap was then removed in order to add 0.483 g of 1,4,5,8-naphthalenetetracarboxylic dianhydride (1.8 mmol) previously dissolved in an organic solvent, N,N-dimethylformamide (DMF). The flask containing the mixture was then covered and kept at a temperature of 150° C. under stirring (500 rpm) for a period of 26 hours. The mixture was then cooled. The solid thus produced was collected, washed with tetrahydrofuran (THF) and dried under vacuum in order to sublimate unreacted sulfur. Finally, the percentage of sulfur in the active electrode material (polymer) produced was determined by elemental analysis. The active electrode material of the present example comprised 20% of sulfur.

g) Copolymerization of 1,4,5,8-Naphthalenetetracarboxylic Dianhydride, 4-Aminophenyl Disulfide and Sulfur (30% by Weight)

The synthesis of an active electrode material was carried out according to the process presented in Example 1(f). The masses of elemental sulfur $S_8$ and 4-aminophenyl disulfide for the synthesis of the amino-sulfur co-monomer were respectively 2.052 g (8 mmol) and 1.987 g (8 mmol) and the mass of 1,4,5,8-naphthalenetetracarboxylic dianhydride for the polycondensation was of 2.145 g (8 mmol). The active electrode material thus produced comprised 30% by weight of sulfur as determined by elemental analysis.

h) Copolymerization of Pyromellitic Dianhydride and Cystamine by Polycondensation Followed by the Insertion of Sulfur (20% by Weight)

The synthesis of the copolymer was carried out in a 100 mL flask equipped with a magnetic bar. The material was prepared by combining 7.614 g of cystamine dihydrochloride (0.5 mol) and 10.91 g of pyromellitic dianhydride (0.5 mol). The mixture was then heated to a temperature of 150° C. under stirring (500 rpm) for a period of 26 hours. The mixture was then cooled. The solid thus produced was recovered, washed with tetrahydrofuran (THF). 1.204 g of this copolymer was then dispersed in NMP and 1.856 g of elemental sulfur $S_8$ (50% by weight) was added. The flask was then sealed and put under a flow of inert gas ($N_2$). Once the flask's atmosphere was purged, the mixture was heated to a temperature of 185° C. under constant stirring at 500 rpm for about 20 hours. The mixture was then cooled. The solid thus produced was recovered, washed with tetrahydrofuran (THF) and dried under vacuum to sublimate unreacted sulfur. Finally, the sulfur percentage in the active electrode material (polymer) produced was determined by elemental analysis. The active electrode material of the present example comprised 20% of sulfur.

Example 2—Preparation of Electrochemical Cells a) Cathode

The cathode material is composed of 60% by weight of the hybrid organosulfide electrode material, i.e. the polyimide-co-polysulfide of Example 1, or the polyimide disulfide (reference), 30% by weight of conductive carbon (15% VGCF and 15% Ketjen™ 600 carbon) and 10% by weight of binder, namely polyvinylidene fluoride (PVDF) dissolved in N-methyl-2-pyrrolidone (NMP). The current collector is aluminum. The solvent is evaporated after spreading.

b) Electrolyte

The electrolyte consists of a 1M solution of lithium bis(trifluoromethanesulfonyl)imide (LiTFSI) dissolved in a mixture of dimethoxyethane (DME) and 1,3-dioxolane (DME/DOL), and of lithium nitrate (1%, $LiNO_3$).

c) Anode

The anode is composed of metallic lithium in the form of a thin film.

d) Electrochemical Cell

Cells are thus prepared with the following elements:

Li/Electrolyte/Cathode/Al

Cell 1

Cell 1 comprises the reference cathode comprising the disulfide polyimide presented in Example 2 (a), the electrolyte presented in Example 2 (b), and an anode composed of metallic lithium presented in Example 2 (c).

Cell 2

Cell 2 comprises the cathode presented in Example 2 (a) which comprises the electrode material of Example 1 (c), the electrolyte presented in Example 2 (b) and an anode composed of metallic lithium presented in Example 2 (c).

Cell 3

Cell 3 comprises the cathode presented in Example 2 (a) which comprises the electrode material of Example 1 (d), the electrolyte presented in Example 2 (b) and an anode composed of metallic lithium presented in Example 2 (c).

Cell 4

Cell 4 comprises the cathode presented in Example 2 (a) which comprises the electrode material of Example 1 (e), the electrolyte presented in Example 2 (b) and an anode composed of metallic lithium presented in Example 2 (c).

Cell 5

Cell 5 comprises the cathode presented in Example 2 (a) which comprises the electrode material of Example 1 (b), the electrolyte presented in Example 2 (b) and an anode composed of metallic lithium presented in Example 2 (c).

Cell 6

Cell 6 comprises the cathode presented in Example 2 (a) which comprises the electrode material of Example 1 (f), the electrolyte presented in Example 2 (b) and an anode composed of metallic lithium presented in Example 2 (c).

Cell 7

Cell 7 comprises the cathode presented in Example 2 (a) which comprises the electrode material of Example 1 (g), the electrolyte presented in Example 2 (b) and an anode composed of metallic lithium presented in Example 2 (c).

Cell 8

Cell 8 comprises the cathode presented in Example 2 (a) which comprises the electrode material of Example 1 (h) (without addition of sulfur), the electrolyte presented in Example 2 (b) and an anode composed of metallic lithium presented in Example 2 (c).

Cell 9

Cell 9 comprises the cathode presented in Example 2 (a) which comprises the electrode material of Example 1 (a) containing 20% by weight of sulfur, the electrolyte presented in Example 2 (b) and an anode composed of metallic lithium presented in Example 2 (c).

Example 3—Electrochemical Properties

Figure 1B:
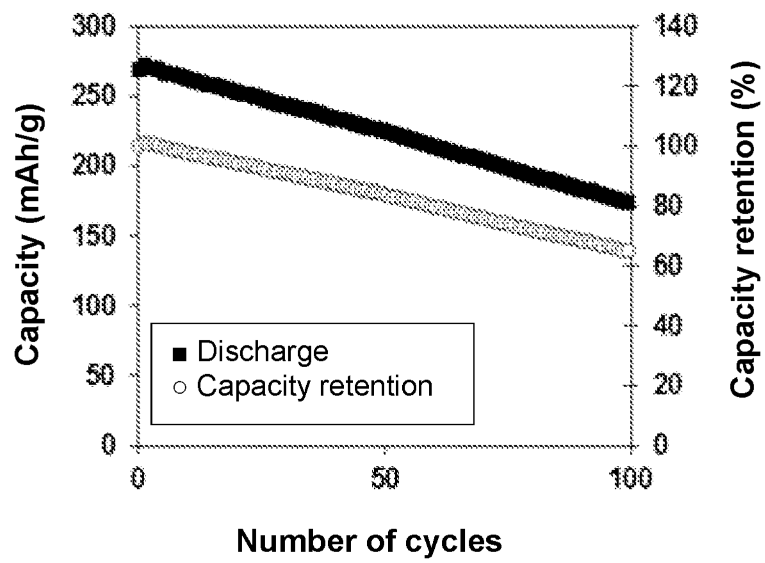

Electrochemical measurements were performed on the electrochemical cells of Example 2(d). As demonstrated in FIG. 1, the presence of sulfur inserted into the disulfide bond allows to obtain a better performing material having improved capacity and cyclability. FIGS. 1 (A) and 1 (B) respectively show the capacity and capacity retention results as a function of the number of cycles for Cell 1 (reference) and for Cell 2. Indeed, by comparing the results presented a significant improvement in capacity and percentage of capacity retention can be observed for Cell 2 compared to Cell 1.

Figure 2:
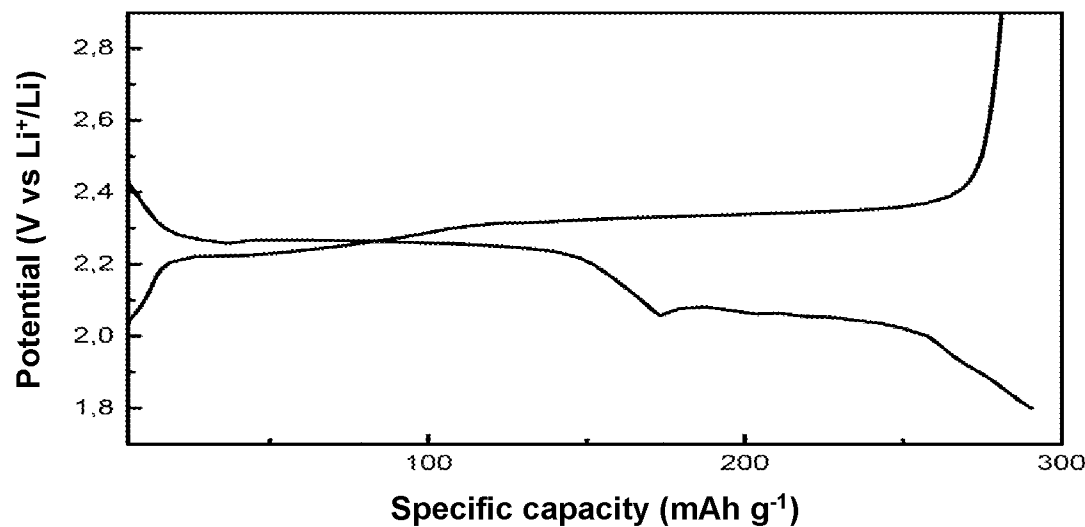
FIG. 2 shows a galvanostatic curve presenting the capacity results (mAh/g) as a function of voltage (V) for the first cycle at C/10 for Cell 2 which includes the copolymer presented in Example 1 (c).

FIG. 2 presents the capacity results as a function of the voltage for the first cycle in C/10 for Cell 2 wherein the contribution of the polymer to the capacity of the new material can be observed by the presence of the plateau at about 2.2 V. Cell 2 obtains a first discharge capacity of 290 mAh $g^{-1}$ in C/10 and a percentage of capacity retention of 65% after 100 cycles in C/2.

Figure 3:
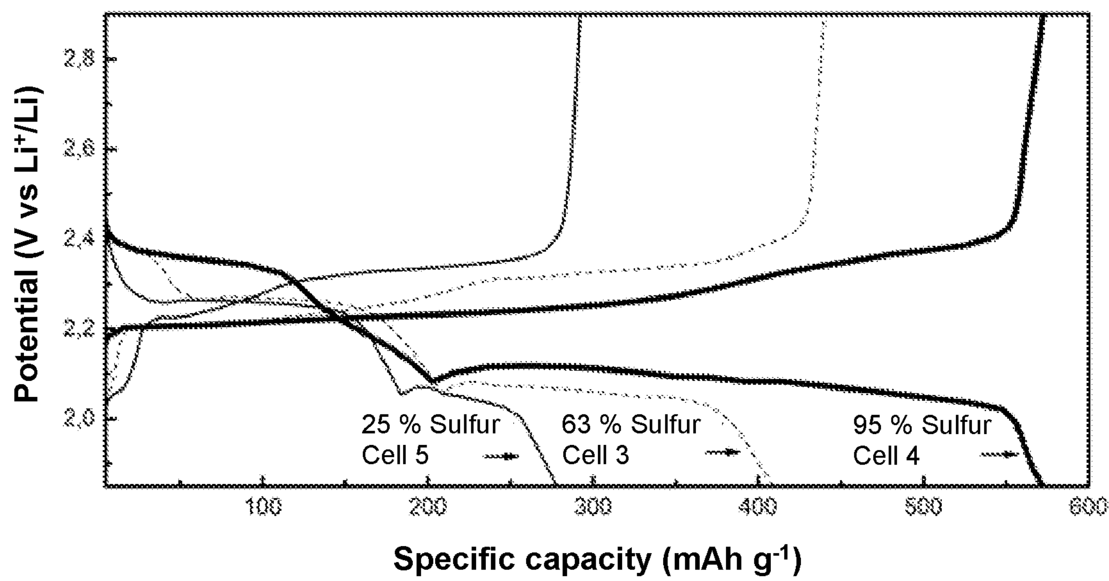
FIG. 3 shows galvanostatic curves presenting the capacity results (mAh/g) as a function of voltage (V) for the first charge-discharge cycle for Cell 3 (dotted line), Cell 4 (thick solid line) and Cell 5 (thin solid line).

FIG. 3 presents the first charge-discharge curve for Cells 3 to 5 in C/10, where the initial capacity varies depending on the nature of the active material. The capacity obtained with Cell 3, Cell 4 and Cell 5 is respectively 407 mAh $g^{-1}$, 570 mAh $g^{-1}$ and 277 mAh $g^{-1}$.

Figure 4:
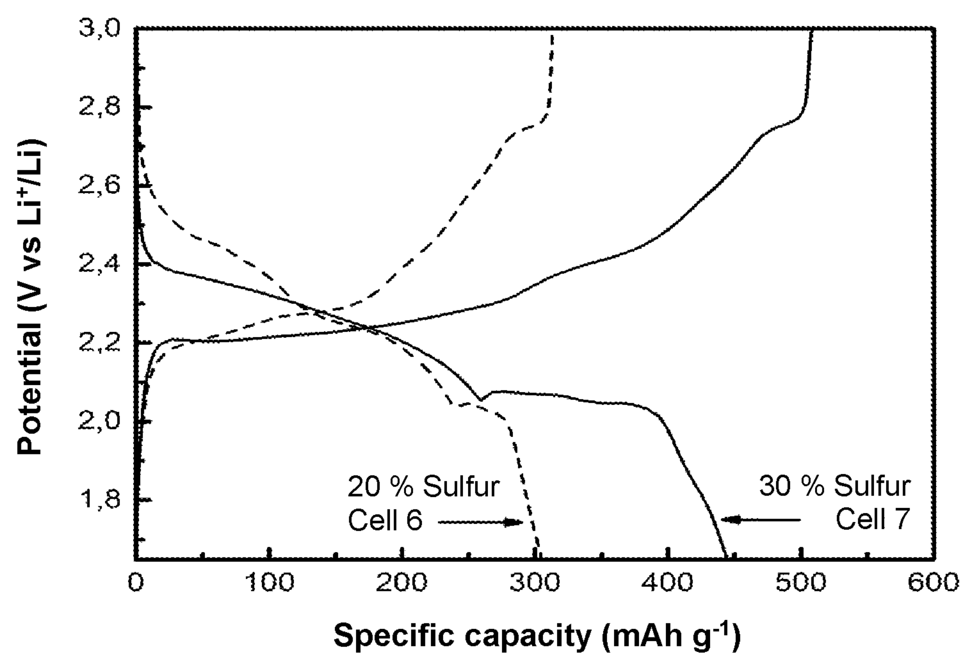
FIG. 4 shows galvanostatic curves presenting the capacity results (mAh/g) as a function of voltage (V) for the first charge-discharge cycle for Cell 6 (dotted line) and for Cell 7 (solid line).

FIG. 4 presents the capacity results as a function of voltage for the first cycle in C/10 for Cells 6 and 7 wherein the contribution of sulfur to the capacity of the new material can be observed by the presence of the plateau at around 2.05 V. Cell 6 obtains a first discharge capacity of 305 mAh $g^{-1}$ in C/10 and a percentage of capacity retention of 91% after 50 cycles in C/2. For Cell 7, the capacity of the first discharge is 443 mAh $g^{-1}$ in C/10 and has a percentage of capacity retention of 75% after 50 cycles.

Figure 5A:
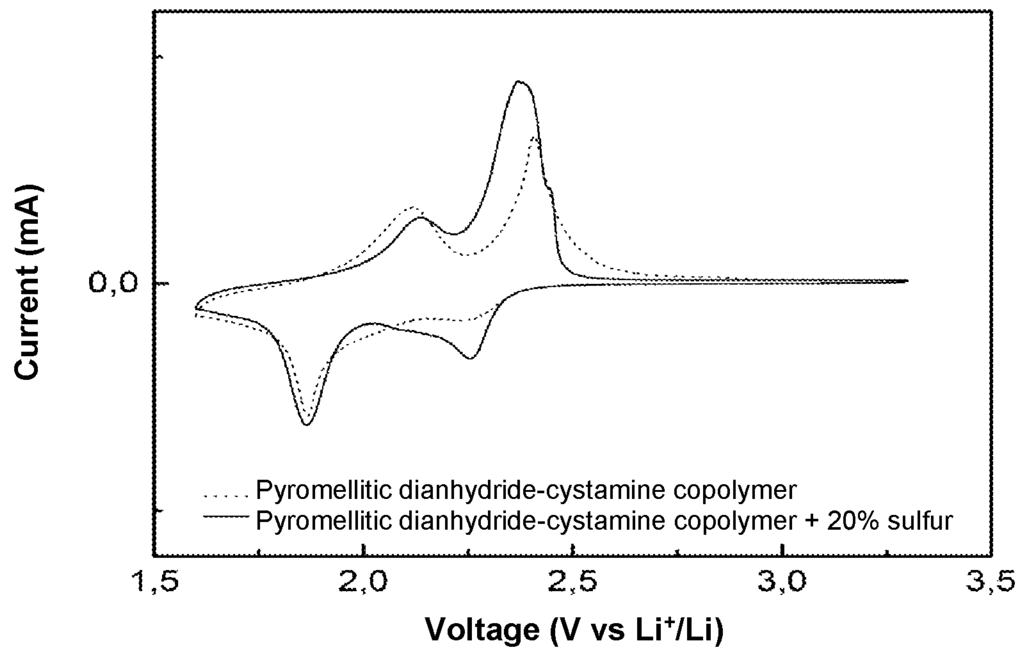
FIG. 5A shows cyclic voltammetry curves for Cells 8 (dotted line) and 9 (solid line) which include the active material of Example 1 (h)
Figure 5B:
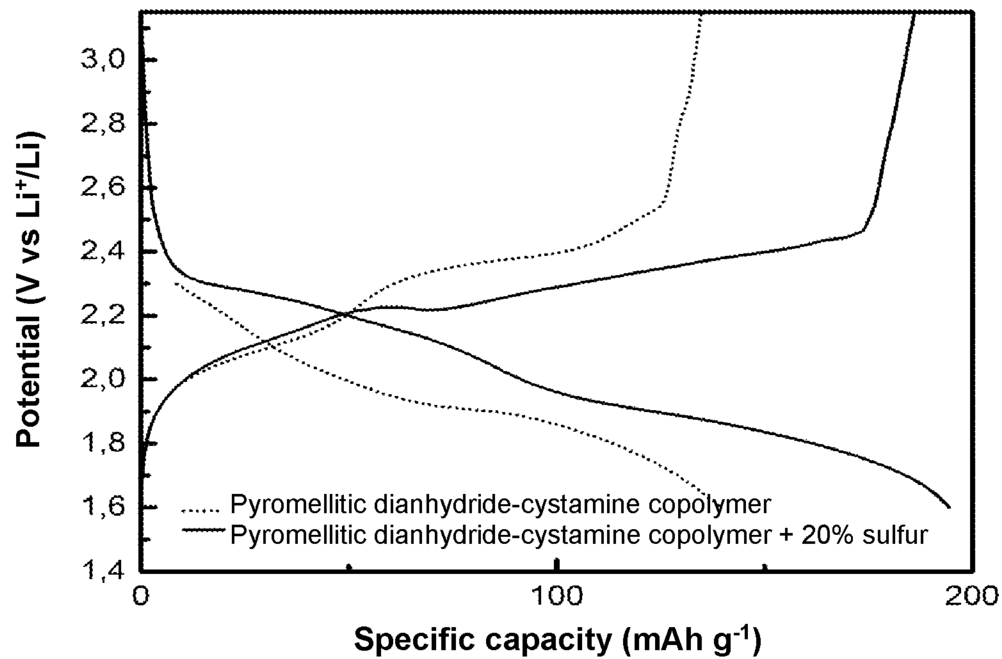
FIG. 5B shows galvanostatic curves presenting the capacity results (mAh/g) as a function of voltage (V) for the first charge-discharge cycle of Cells 8 and 9.
Figure 6:
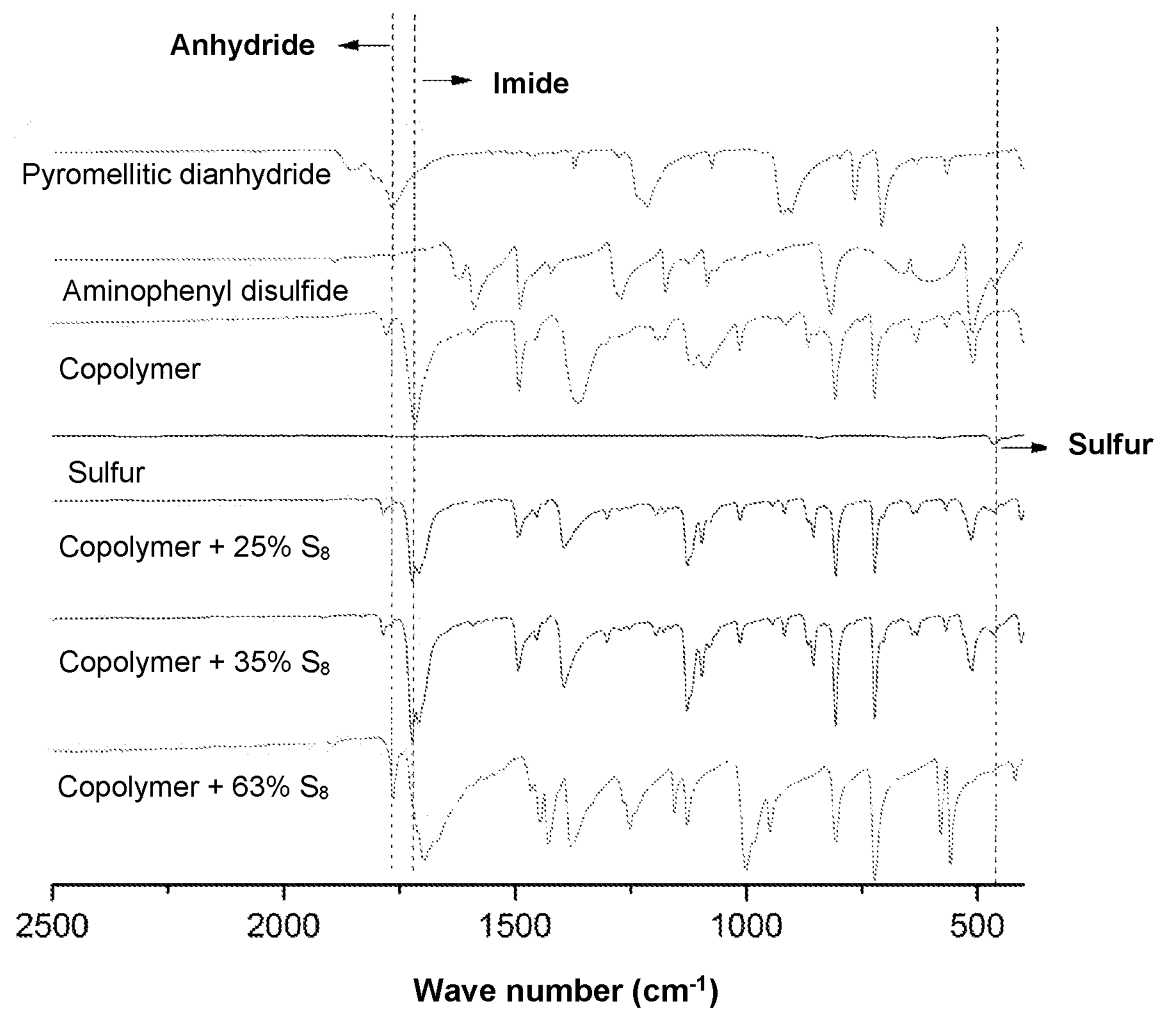
FIG. 6 presents the infrared transmission spectra of the active electrode materials presented in Examples 1 (b), (c), (d), of the monomers used in the copolymerization, of the imide copolymer without the addition of sulfur and of elemental sulfur.

FIG. 5 (*a*) presents the cyclic voltammograms for Cells 8 and 9. It is possible to see the effect of sulfur addition on the intensity of the oxidation and reduction peaks. Furthermore, an increase in capacity is obtained when adding sulfur as can be observed in FIG. 5 (*b*). Cell 8 obtains an initial discharge capacity of 138 mAh $g^{-1}$ in C/10 and a percentage of capacity retention of 37% after 100 cycles in C/2. For Cell 9, the capacity obtained for the first discharge is 195 mAh $g^{-1}$ in C/10 and has a percentage of capacity retention of 50% after 100 cycles Example 4—Characterization and Determination of the Material Composition The composition of the materials presented in Example 1 was determined using transmission infrared spectroscopy spectra. FIG. 6 presents the infrared transmission spectra of the active electrode materials presented in Examples 1 (b), (c), (d) as well as the spectra of the monomers used during the copolymerization, of the imide copolymer without the addition of sulfur and the spectrum of elemental sulfur.

Figure 7:
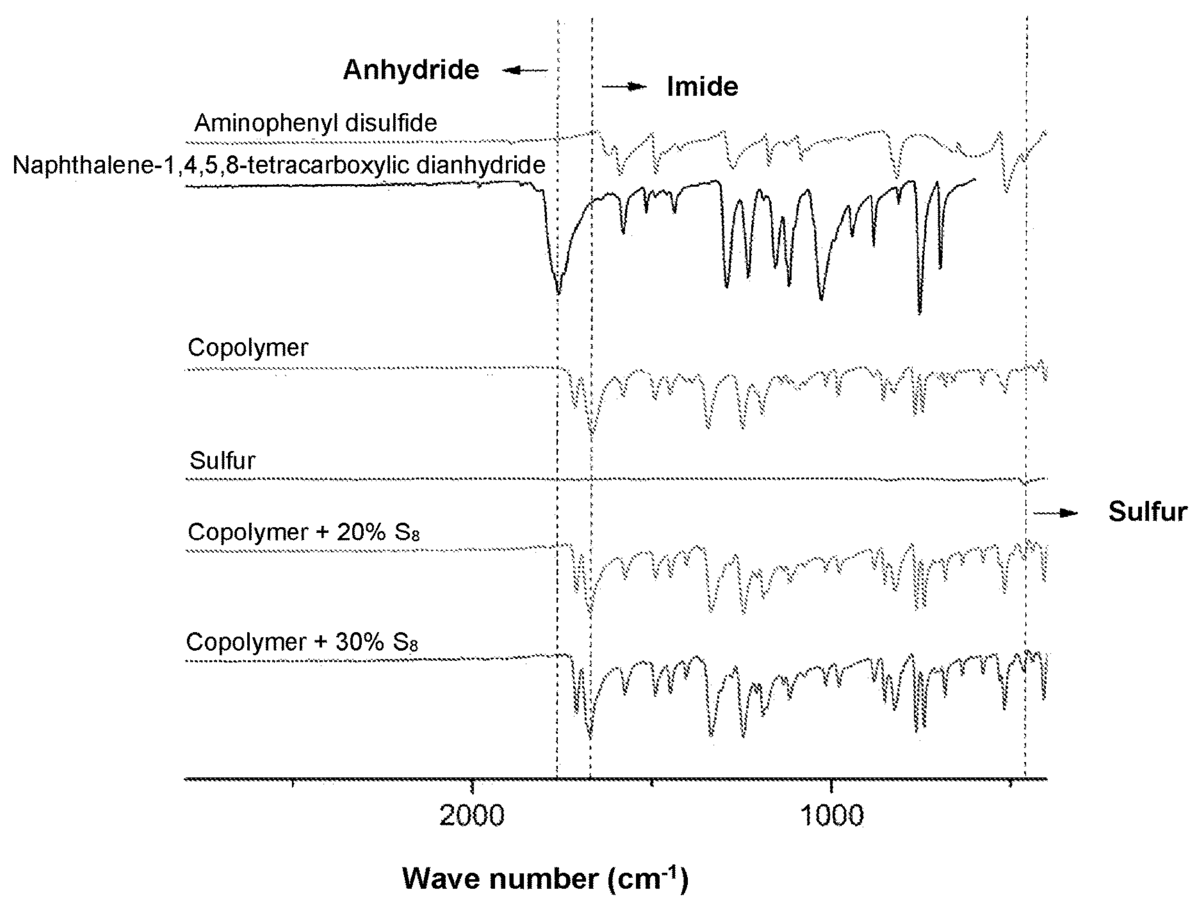
FIG. 7 shows infrared transmission spectra of the active electrode materials presented in Examples 1 (f) and 1 (g), of the monomers used in copolymerization, of elemental sulfur and of the copolymer without addition of sulfur.

FIG. 7 presents the infrared transmission spectra of the active electrode materials presented in Examples 1(f) and 1(g) as well as the spectra of the monomers used in the copolymerization, of elemental sulfur and of the sulfur-free copolymer.

Figure 8:
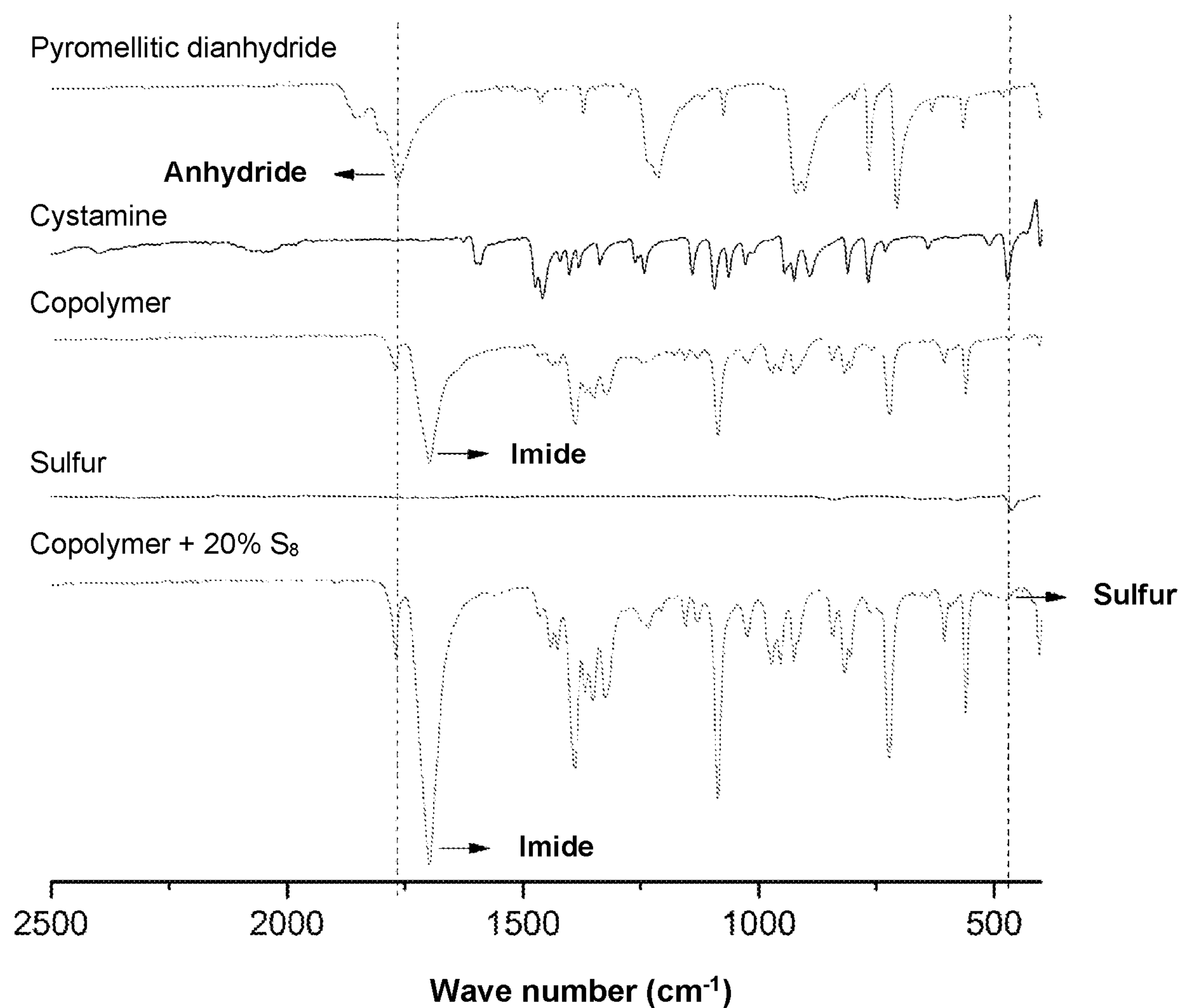
FIG. 8 shows infrared transmission spectra of the active material presented in Example 1 (h), of the monomers used in copolymerization, of elemental sulfur and of the copolymer without addition of sulfur.

FIG. 8 presents the infrared transmission spectra of the active electrode material presented in Example 1 (h) as well as the spectra of the monomers used in the copolymerization, of elemental sulfur and of the copolymer without added sulfur.

Example 5—Ionic Conductivities a) Measurement of the Ionic Conductivity of the Material Presented in Example 1(c)

Ion conductivity results were obtained for the copolymer presented in Example 1 (c). To do this, the copolymer presented in Example 1 (c) was mixed in an organic solvent (NMP) with a lithium salt (LiTFSI) and with a binder (PVDF). The homogeneous dispersion was spread on a stainless-steel foil having a thickness of 27 μm. The film was then dried for 16 hours at a temperature of 120° C. The NMP being evaporated, a ratio (copolymer:LiTFSI:PVDF) of 70:20:10 (mass percentage) was obtained.

The resulting film was then placed between two stainless steel electrodes and assembled into a coin cell to measure the ionic conductivity. Electrochemical impedance spectroscopy was performed between 800 kHz and 100 Hz at various temperatures (25° C., 40° C., 60° C. and 80° C.).

Figure 9:
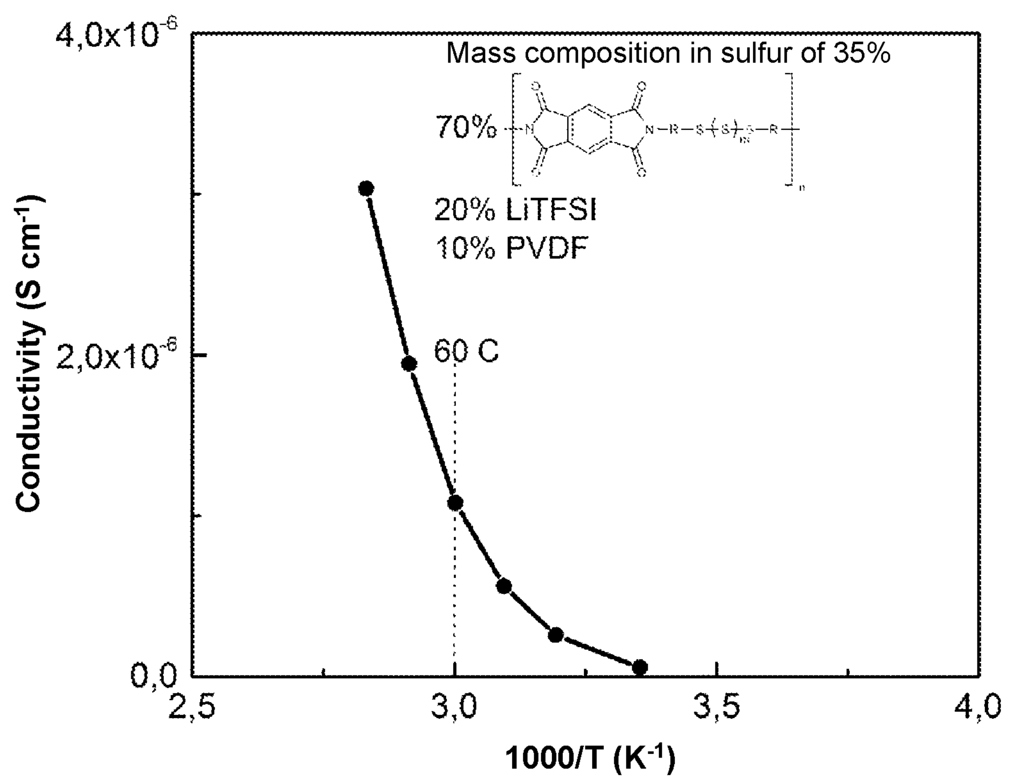
FIG. 9 shows ionic conductivity results (S $cm^{-1}$) for the copolymer presented in Example 1 (c) as a function of the temperature ($K^{-1}$).

The graph in FIG. 9 presents the conductivity values measured as a function of temperature. A maximum value of $3.06\times10^{-6}$ S·cm$^{-1}$ was obtained at a temperature of 80° C.

b) Measurement of the Ionic Conductivity of the Material Presented in Example 1(d)

Figure 10:
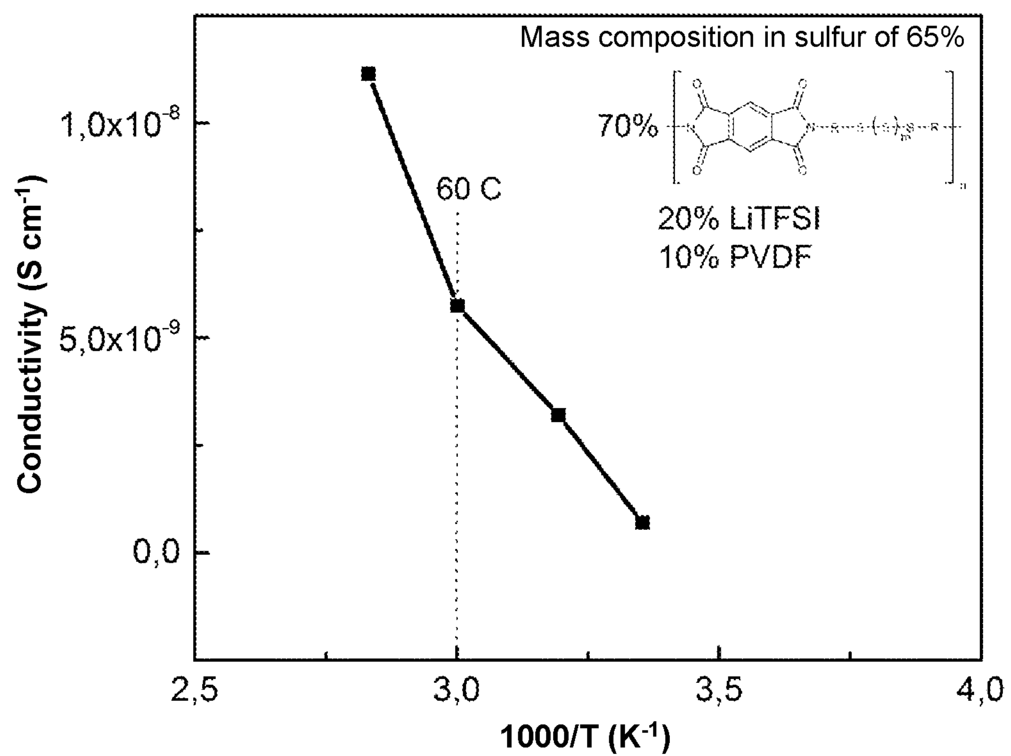
FIG. 10 shows ionic conductivity results (S $cm^{-1}$) for the copolymer presented in Example 1 (d) as a function of the temperature ($K^{-1}$).

The conductivity as a function of the temperature of the sulfur-containing copolymer presented in Example 1(d), was measured using the method and ratios presented in Example 5(a). The ionic conductivity results are presented in FIG. 10. A maximum value of $1.12\times10^{-8}$ S·cm$^{-1}$ was obtained at a temperature of 80° C.

c) Measurement of the Ionic Conductivity of the Material Presented in Example 1(g)

Figure 11A:
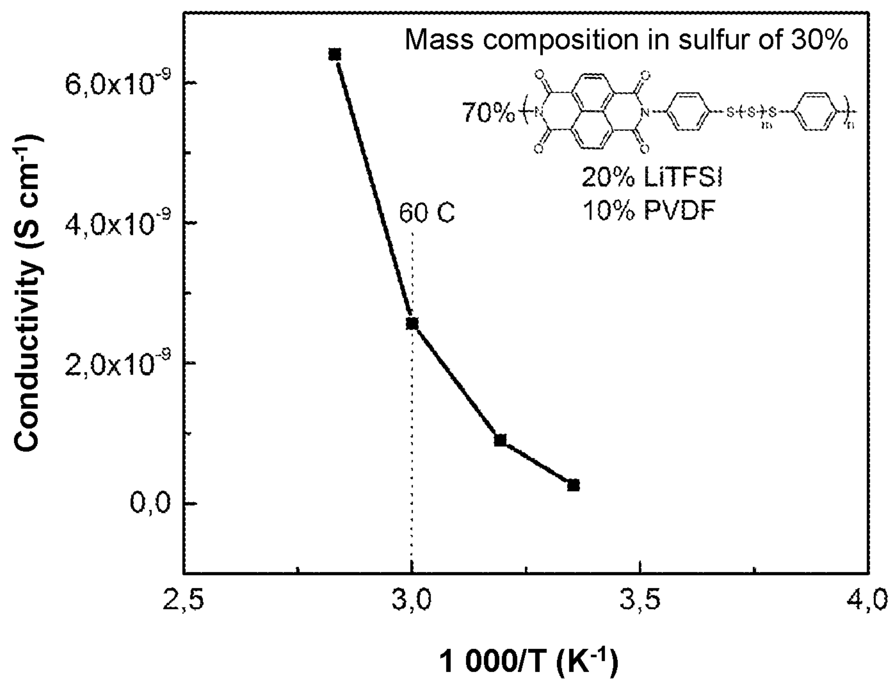
FIGS. 11A-11B show ionic conductivity results (S $cm^{-1}$) for the copolymer presented in Example 1 (g) as a function of the temperature ($K^{-1}$). The ionic conductivity values for a film as described in Example 5 (c) are presented in (A); and the ionic conductivity values in the form of pressed powder as described in Example 5 (d) are presented in (B).
Figure 11B:
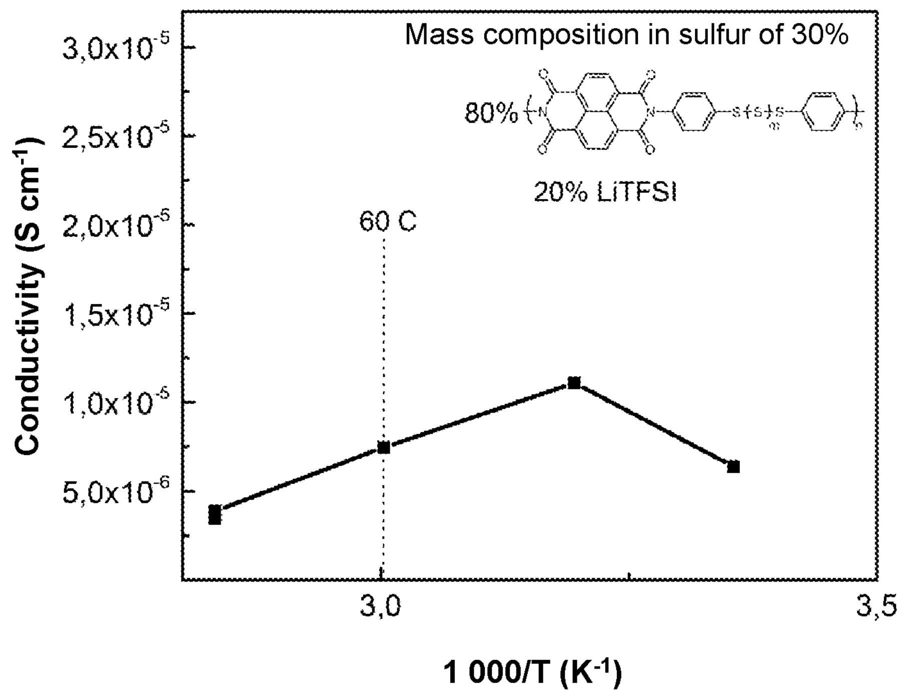

The conductivity as a function of the temperature of the sulfur-containing copolymer presented in Example 1(g) was measured using the method and ratios presented in Example 5(a). The results are shown in FIG. 11 (A). A maximum value of $6.43\times10^{-9}$ S·cm$^{-1}$ was obtained at a temperature of 80° C.

d) Measurement of the Ionic Conductivity of the Material Presented in Example 1(g)

The ionic conductivity was measured a second time for the sulfur-containing copolymer presented in Example 1(g). To do this, the sulfur-containing copolymer presented in Example 1(g) was mixed with 20% by weight of a lithium salt (LiTFSI). This solid mixture was pressed between two stainless steel electrodes at a temperature of 150° C. for a period of 30 minutes. Electrochemical impedance spectroscopy was then measured between 800 kHz and 100 Hz at various temperatures (25° C., 40° C., 60° C. and 80° C.). The results are presented in FIG. 11(B). A maximum ionic conductivity of $1.1\times10^{-5}$ S·cm$^{-1}$ was obtained at a temperature of 40° C.

Numerous modifications could be made to one or another of the embodiments described above without departing from the scope of the present invention as contemplated. Any references, patents or scientific literature documents referred to in the present application are incorporated herein by reference in their entirety for all purposes.

The invention claimed is:

1. A compound Compound-of Formula II:

Formula II

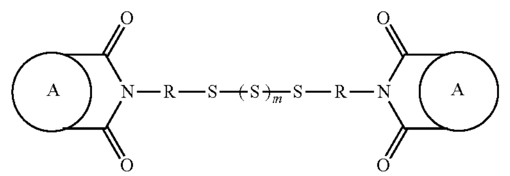

wherein:

A is an unsaturated group allowing the delocalization of electrons selected from substituted or unsubstituted aryl and heteroaryl groups, and their fused or unfused polycyclic equivalents;

R is an organic linking group selected from unsubstituted linear or branched $C_{2-6}$alkylene, substituted or unsubstituted linear or branched $C_{2-6}$alkyleneoxy, substituted or unsubstituted linear or branched $C_{2-6}$alkyleneglycol, substituted or unsubstituted linear or branched $C_{2-6}$alkyleneoxy$C_{2-6}$alkylene, substituted or unsubstituted linear or branched poly ($C_{2-6}$alkyleneglycol), substituted or unsubstituted $C_{6-12}$arylene, substituted or unsubstituted $C_{3-12}$cycloalkylene, substituted or unsubstituted $C_{5-12}$heteroarylene, and substituted or unsubstituted $C_{3-12}$heterocycloalkylene; and m represents the number of sulfur atoms inserted into the disulfide bond of the compound and cannot be zero.

2. The compound according to claim 1, wherein A is selected from benzene, naphthalene, perylene, and biphenyl groups.

3. The compound according to claim 1, wherein R is selected from the groups benzene, ethylene, propylene, poly (ethylene glycol), poly (propylene glycol), and copolymers of ethylene glycol and propylene glycol.

4. The compound according to claim 1, wherein m is $0<m\leq 8$.

5. The compound according to claim 1, wherein m is $1\leq m\leq 6$.

6. The compound according to claim 1, wherein m is $1\leq m\leq 4$.

7. The compound according to claim 1, the compound being of Formula II (a):

Formula II(a)

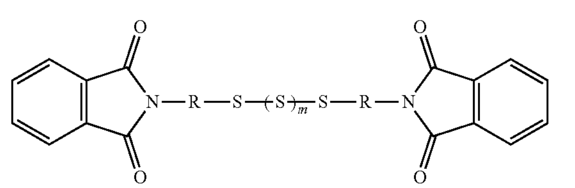

wherein R and m are as defined in claim 1.

8. The compound according to claim 1, the compound being of Formula II (b):

Formula II(b)

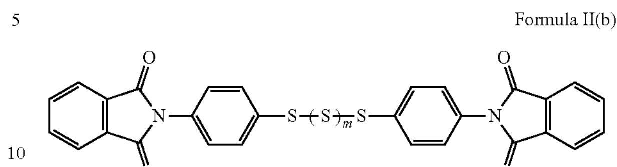

wherein m is as defined in claim 1.

9. An electrode material comprising a compound as defined in claim 1, and optionally elemental sulfur and/or a conductive material, a binder, or a combination of both.

10. The electrode material according to claim 9, wherein the conductive material is selected from carbon black, graphite, graphene, carbon fibers, and carbon nanotubes, or a combination of at least two thereof.

11. The electrode material according to claim 9, wherein the binder is a polymeric binder of polyether type, a fluorinated polymer, or a water-soluble binder.

12. The electrode material according to claim 11, wherein:

the polymeric binder of polyether type is linear, branched and/or crosslinked and is based on poly (ethylene oxide) (PEO), poly (propylene oxide) (PPO), a mixture of the two, for an EO/PO co-polymer), and optionally comprises crosslinkable units;

the fluorinated polymer binder is PVDF (polyvinylidene fluoride) or PTFE (polytetrafluoroethylene); or the water-soluble binder is SBR (styrene-butadiene rubber), NBR (acrylonitrile-butadiene rubber), HNBR (hydrogenated NBR), CHR (epichlorohydrin rubber), or ACM (acrylate rubber), optionally comprising CMC (carboxymethyl cellulose).

13. A positive electrode comprising an electrode material as defined in claim 9 applied on a current collector.

14. An electrochemical cell comprising a cathode, an electrolyte and an anode, wherein the cathode comprises an electrode material as defined in claim 9.

15. A lithium battery comprising an electrochemical cell as defined in claim 14.

16. An electrolyte comprising a compound as defined in claim 1, and optionally elemental sulfur.

17. The electrolyte according to claim 16, the electrolyte being a liquid electrolyte comprising a salt in a solvent or a gel electrolyte comprising a salt in a solvent and optionally a solvating polymer or a solid polymer electrolyte (SPE) comprising a salt in a solvating polymer.

18. The electrolyte according to claim 17, wherein the solvent of the liquid or gel electrolyte is a polar aprotic solvent selected from ethylene carbonate (EC), diethyl carbonate (DEC), propylene carbonate (PC), dimethyl carbonate (DMC), ethylmethyl carbonate (EMC), γ-butyrolactone (γ-BL), vinylene carbonate (VC), methyl butyrate (MB), γ-valerolactone (γ-VL), 1,2-dimethoxyethane (DME), 1,2-diethoxyethane (DEE), 2-methyltetrahydrofuran, dimethylsulfoxide, formamide, acetamide, dimethylformamide, dioxolane, acetonitrile, propylnitrile, nitromethane, ethylmonoglyme, trimethoxymethane, dioxolane derivatives, sulfolane, methylsulfolane, propylene carbonate derivatives, tetrahydrofuran, and mixtures thereof.

19. The electrolyte according to claim 17, wherein the salt of the liquid, gel or solid polymer electrolyte is a lithium salt selected from lithium hexafluorophosphate ($LiPF_6$), lithium bis(trifluoromethanesulfonyl) imide (LiTFSI), lithium bis (fluorosulfonyl) imide (LiFSI), lithium 2-trifluoromethyl-4,5-dicyanoimidazolate (LiTDI), lithium 4,5-dicyano-1,2,3-triazolate (LiDCTA), lithium bis(pentafluoroethylsulfonyl) imide (LiBETI), lithium tetrafluoroborate ($LiBF_4$), lithium bis (oxalato)borate (LiBOB), lithium nitrate ($LiNO_3$), lithium chloride (LiCl), lithium bromide (LiBr), lithium fluoride (LiF), lithium perchlorate ($LiClO_4$), lithium hexafluoroarsenate ($LiAsF_6$), lithium trifluoromethanesulfonate ($LiSO_3CF_3$) (LiTf), lithium tris(pentafluoroethyl) trifluorophosphate $Li[PF_3(CF_2CF_3)_3]$ (LiFAP), lithium tetrakis (trifluoroacetoxy)borate $Li[B(OCOCF_3)_4]$ (LiTFAB), lithium bis(1,2-benzenediolato (2-)-O,O')borate $Li[B(C_6O_2)_2]$ (LBBB) and combinations thereof.

20. The electrolyte according to claim 16, the compound being an additive.

21. The electrolyte according to claim 16, the electrolyte further comprising an electrolyte binder.

22. An electrochemical cell comprising a cathode, an anode and an electrolyte as defined in claim 16.

23. A lithium battery comprising an electrochemical cell as defined in claim 22.

* * * * *